United States Patent
Pattison et al.

(10) Patent No.: US 11,944,348 B2
(45) Date of Patent: Apr. 2, 2024

(54) SURGICAL ACCESS DEVICE INCLUDING AN ANCHOR HAVING A SUTURE RETENTION MECHANISM

(71) Applicant: Covidien LP, Mansfield, MA (US)

(72) Inventors: Douglas M. Pattison, Bristol, CT (US); Kevin M. Desjardin, Prospect, CT (US)

(73) Assignee: Covidien LP, Mansfield, MA (US)

( * ) Notice: Subject to any disclaimer, the term of this patent is extended or adjusted under 35 U.S.C. 154(b) by 302 days.

(21) Appl. No.: 17/224,398

(22) Filed: Apr. 7, 2021

(65) Prior Publication Data
US 2022/0323103 A1    Oct. 13, 2022

(51) Int. Cl.
A61B 17/34    (2006.01)
A61B 17/04    (2006.01)

(52) U.S. Cl.
CPC ...... *A61B 17/3423* (2013.01); *A61B 17/0469* (2013.01); *A61B 17/0493* (2013.01); *A61B 2017/3429* (2013.01)

(58) Field of Classification Search
CPC ............ A61B 17/3423; A61B 17/3439; A61B 2017/3486
See application file for complete search history.

(56) References Cited

U.S. PATENT DOCUMENTS

| | | |
|---|---|---|
| 397,060 A | 1/1889 | Knapp |
| 512,456 A | 1/1894 | Sadikova |
| 1,213,005 A | 1/1917 | Pillsbury |
| 2,912,981 A | 11/1959 | Keough |
| 2,936,760 A | 5/1960 | Gains |
| 3,039,468 A | 6/1962 | Price |
| 3,050,066 A | 8/1962 | Koehn |
| 3,253,594 A | 5/1966 | Matthews et al. |
| 3,397,699 A | 8/1968 | Kohl |
| 3,545,443 A | 12/1970 | Ansari et al. |

(Continued)

FOREIGN PATENT DOCUMENTS

| | | |
|---|---|---|
| EP | 0480653 A1 | 4/1992 |
| EP | 0610099 A2 | 8/1994 |

(Continued)

OTHER PUBLICATIONS

Extended European Seach Report dated Jul. 29, 2022 issued in corresponding EP Appln. No. 22164758.

(Continued)

*Primary Examiner* — Nicholas W Woodall
(74) *Attorney, Agent, or Firm* — Carter, DeLuca & Farrell LLP

(57) ABSTRACT

A surgical access device includes a cannula body, an anchor, and a first suture retention mechanism. The cannula body includes a housing and an elongated portion extending distally from the housing. The elongated portion defines a longitudinal axis and a channel extending therethrough. The anchor is disposed in mechanical cooperation with the elongated portion of the cannula body and is longitudinally translatable relative to the elongated portion. The first suture retention mechanism extends laterally from the anchor. A suture-receiving channel is defined between a portion of the suture retention mechanism and a portion of the anchor.

20 Claims, 7 Drawing Sheets

(56) References Cited

U.S. PATENT DOCUMENTS

| | | | |
|---|---|---|---|
| 3,713,447 A | 1/1973 | Adair | |
| 3,774,596 A | 11/1973 | Cook | |
| 3,800,788 A | 4/1974 | White | |
| 3,882,852 A | 5/1975 | Sinnreich | |
| 3,896,816 A | 7/1975 | Mattler | |
| 3,961,632 A | 6/1976 | Moossun | |
| RE29,207 E | 5/1977 | Bolduc et al. | |
| 4,083,369 A | 4/1978 | Sinnreich | |
| 4,217,889 A | 8/1980 | Radovan et al. | |
| 4,243,050 A | 1/1981 | Littleford | |
| 4,276,874 A | 7/1981 | Wolvek et al. | |
| 4,312,353 A | 1/1982 | Shahbabian | |
| 4,327,709 A | 5/1982 | Hanson et al. | |
| 4,345,606 A | 8/1982 | Littleford | |
| 4,411,654 A | 10/1983 | Boarini et al. | |
| 4,416,267 A | 11/1983 | Garren et al. | |
| 4,490,137 A | 12/1984 | Moukheibir | |
| 4,496,345 A | 1/1985 | Hasson | |
| 4,574,806 A | 3/1986 | McCarthy | |
| 4,581,025 A | 4/1986 | Timmermans | |
| 4,596,554 A | 6/1986 | Dastgeer | |
| 4,596,559 A | 6/1986 | Fleischhacker | |
| 4,608,965 A | 9/1986 | Anspach, Jr. et al. | |
| 4,644,936 A | 2/1987 | Schiff | |
| 4,654,030 A | 3/1987 | Moll et al. | |
| 4,685,447 A | 8/1987 | Iversen et al. | |
| 4,701,163 A | 10/1987 | Parks | |
| 4,738,666 A | 4/1988 | Fuqua | |
| 4,769,038 A | 9/1988 | Bendavid et al. | |
| 4,772,266 A | 9/1988 | Groshong | |
| 4,779,611 A | 10/1988 | Grooters et al. | |
| 4,784,133 A | 11/1988 | Mackin | |
| 4,793,348 A | 12/1988 | Palmaz | |
| 4,798,205 A | 1/1989 | Bonomo et al. | |
| 4,800,901 A | 1/1989 | Rosenberg | |
| 4,802,479 A | 2/1989 | Haber et al. | |
| 4,813,429 A | 3/1989 | Eshel et al. | |
| 4,840,613 A | 6/1989 | Balbierz | |
| 4,854,316 A | 8/1989 | Davis | |
| 4,861,334 A | 8/1989 | Nawaz | |
| 4,865,593 A | 9/1989 | Ogawa et al. | |
| 4,869,717 A | 9/1989 | Adair | |
| 4,888,000 A | 12/1989 | McQuilkin et al. | |
| 4,899,747 A | 2/1990 | Garren et al. | |
| 4,917,668 A | 4/1990 | Haindl | |
| 4,931,042 A | 6/1990 | Holmes et al. | |
| 4,955,895 A | 9/1990 | Sugiyama et al. | |
| 5,002,557 A | 3/1991 | Hasson | |
| 5,009,643 A | 4/1991 | Reich et al. | |
| 5,030,206 A | 7/1991 | Lander | |
| 5,030,227 A | 7/1991 | Rosenbluth et al. | |
| 5,074,871 A | 12/1991 | Groshong | |
| 5,098,392 A | 3/1992 | Fleischhacker et al. | |
| 5,104,383 A | 4/1992 | Shichman | |
| 5,116,318 A | 5/1992 | Hillstead | |
| 5,116,357 A | 5/1992 | Eberbach | |
| 5,122,122 A | 6/1992 | Allgood | |
| 5,122,155 A | 6/1992 | Eberbach | |
| 5,137,512 A | 8/1992 | Burns et al. | |
| 5,141,494 A | 8/1992 | Danforth et al. | |
| 5,141,515 A | 8/1992 | Eberbach | |
| 5,147,302 A | 9/1992 | Euteneuer et al. | |
| 5,147,316 A | 9/1992 | Castillenti | |
| 5,147,374 A | 9/1992 | Fernandez | |
| 5,158,545 A | 10/1992 | Trudell et al. | |
| 5,159,925 A | 11/1992 | Neuwirth et al. | |
| 5,163,949 A | 11/1992 | Bonutti | |
| 5,176,692 A | 1/1993 | Wilk et al. | |
| 5,176,697 A | 1/1993 | Hasson et al. | |
| 5,183,463 A | 2/1993 | Debbas | |
| 5,188,596 A | 2/1993 | Condon et al. | |
| 5,188,630 A | 2/1993 | Christoudias | |
| 5,195,507 A | 3/1993 | Bilweis | |
| 5,201,742 A | 4/1993 | Hasson | |
| 5,201,754 A | 4/1993 | Crittenden et al. | |
| 5,209,725 A | 5/1993 | Roth | |
| 5,215,526 A | 6/1993 | Deniega et al. | |
| 5,215,531 A | 6/1993 | Maxson et al. | |
| 5,222,970 A | 6/1993 | Reeves | |
| 5,226,890 A | 7/1993 | Ianniruberto et al. | |
| 5,232,446 A | 8/1993 | Arney | |
| 5,232,451 A | 8/1993 | Freitas et al. | |
| 5,234,454 A | 8/1993 | Bangs | |
| 5,250,025 A | 10/1993 | Sosnowski et al. | |
| 5,258,026 A | 11/1993 | Johnson et al. | |
| 5,269,753 A | 12/1993 | Wilk | |
| 5,290,249 A | 3/1994 | Foster et al. | |
| 5,308,327 A | 5/1994 | Heaven et al. | |
| 5,309,896 A | 5/1994 | Moll et al. | |
| 5,314,443 A | 5/1994 | Rudnick | |
| 5,318,012 A | 6/1994 | Wilk | |
| 5,330,497 A | 7/1994 | Freitas et al. | |
| 5,342,307 A | 8/1994 | Euteneuer et al. | |
| 5,346,504 A | 9/1994 | Ortiz et al. | |
| 5,359,995 A | 11/1994 | Sewell, Jr. | |
| 5,361,752 A | 11/1994 | Moll et al. | |
| 5,370,134 A | 12/1994 | Chin et al. | |
| 5,383,889 A | 1/1995 | Warner et al. | |
| 5,397,311 A | 3/1995 | Walker et al. | |
| 5,402,772 A | 4/1995 | Moll et al. | |
| 5,407,433 A | 4/1995 | Loomas | |
| 5,431,173 A | 7/1995 | Chin et al. | |
| 5,445,615 A | 8/1995 | Yoon | |
| 5,468,248 A | 11/1995 | Chin et al. | |
| 5,514,091 A | 5/1996 | Yoon | |
| 5,514,153 A | 5/1996 | Bonutti | |
| 5,540,658 A * | 7/1996 | Evans | A61B 17/42 604/101.04 |
| 5,540,711 A | 7/1996 | Kieturakis et al. | |
| 5,607,441 A | 3/1997 | Sierocuk et al. | |
| 5,607,443 A | 3/1997 | Kieturakis et al. | |
| 5,632,761 A | 5/1997 | Smith et al. | |
| 5,656,013 A | 8/1997 | Yoon | |
| 5,667,479 A | 9/1997 | Kieturakis | |
| 5,667,520 A | 9/1997 | Bonutti | |
| 5,704,372 A | 1/1998 | Moll et al. | |
| 5,707,382 A | 1/1998 | Sierocuk et al. | |
| 5,713,869 A | 2/1998 | Morejon | |
| 5,722,986 A | 3/1998 | Smith et al. | |
| 5,728,119 A | 3/1998 | Smith et al. | |
| 5,730,748 A | 3/1998 | Fogarty et al. | |
| 5,730,756 A | 3/1998 | Kieturakis et al. | |
| 5,738,628 A | 4/1998 | Sierocuk et al. | |
| 5,755,693 A | 5/1998 | Walker et al. | |
| 5,762,604 A | 6/1998 | Kieturakis | |
| 5,772,680 A | 6/1998 | Kieturakis et al. | |
| 5,779,728 A | 7/1998 | Lunsford et al. | |
| 5,797,947 A | 8/1998 | Mollenauer | |
| 5,803,901 A | 9/1998 | Chin et al. | |
| 5,810,867 A | 9/1998 | Zarbatany et al. | |
| 5,814,060 A | 9/1998 | Fogarty et al. | |
| 5,836,913 A | 11/1998 | Orth et al. | |
| 5,836,961 A | 11/1998 | Kieturakis et al. | |
| 5,865,802 A | 2/1999 | Yoon et al. | |
| 5,893,866 A | 4/1999 | Hermann et al. | |
| 5,925,058 A | 7/1999 | Smith et al. | |
| 6,361,543 B1 | 3/2002 | Chin et al. | |
| 6,368,337 B1 | 4/2002 | Kieturakis et al. | |
| 6,375,665 B1 | 4/2002 | Nash et al. | |
| 6,379,372 B1 | 4/2002 | Dehdashtian et al. | |
| 6,432,121 B1 | 8/2002 | Jervis | |
| 6,447,529 B2 | 9/2002 | Fogarty et al. | |
| 6,468,205 B1 | 10/2002 | Mollenauer et al. | |
| 6,506,200 B1 | 1/2003 | Chin | |
| 6,514,272 B1 | 2/2003 | Kieturakis et al. | |
| 6,517,514 B1 | 2/2003 | Campbell | |
| 6,527,787 B1 | 3/2003 | Fogarty et al. | |
| 6,540,764 B1 | 4/2003 | Kieturakis et al. | |
| 6,551,270 B1 * | 4/2003 | Bimbo | A61B 17/3462 604/167.03 |
| 6,796,960 B2 | 9/2004 | Cioanta et al. | |
| 8,454,645 B2 | 6/2013 | Criscuolo et al. | |
| 10,751,086 B2 | 8/2020 | Shipp et al. | |

(56) References Cited

U.S. PATENT DOCUMENTS

| | | | |
|---|---|---|---|
| 2003/0171713 A1* | 9/2003 | McFarlane | A61M 39/02 604/93.01 |
| 2005/0043685 A1 | 2/2005 | Schinkel-Fleitmann | |
| 2008/0306442 A1* | 12/2008 | Bardsley | A61B 17/3439 604/164.04 |
| 2009/0182282 A1 | 7/2009 | Okihisa et al. | |
| 2010/0057010 A1 | 3/2010 | Goransson | |
| 2018/0271557 A1* | 9/2018 | Buyda | A61B 17/3423 |
| 2019/0254703 A1 | 8/2019 | Ciampini et al. | |
| 2021/0298739 A1* | 9/2021 | Binmoeller | A61B 17/0469 |

FOREIGN PATENT DOCUMENTS

| | | |
|---|---|---|
| EP | 0880939 A1 | 12/1998 |
| EP | 3861947 | 8/2021 |
| WO | 9206638 A1 | 4/1992 |
| WO | 9218056 A1 | 10/1992 |
| WO | 9221293 A1 | 12/1992 |
| WO | 9221295 A1 | 12/1992 |
| WO | 9309722 A1 | 5/1993 |
| WO | 9721461 A1 | 6/1997 |
| WO | 9912602 A1 | 3/1999 |
| WO | 0126724 A2 | 4/2001 |
| WO | 02096307 A2 | 12/2002 |
| WO | 2004032756 A2 | 4/2004 |
| WO | 2015049391 A1 | 4/2015 |

OTHER PUBLICATIONS

Extended European Search Report dated Jun. 14, 2021 issued in EP Appln. No. 21155396.1.

European Search Report dated Jul. 21, 2015, issued in European Application No. 14 19 9657.

European Office Action corresponing to counterpart Int'l Appln. No. EP 14 19 9657.9 dated Jul. 9, 2016.

CN Office Action dated Jul. 4, 2018 in corresponding CN Patent Application No. 201410855808.8 together with English translation.

Japanese Office Action dated Aug. 27, 2018 in corresponding Japanese Patent Application No. 2014-264805, with English translation.

* cited by examiner

SURGICAL ACCESS DEVICE INCLUDING AN ANCHOR HAVING A SUTURE RETENTION MECHANISM

FIELD

The present disclosure relates to a surgical access device. More particularly, the present disclosure relates to a surgical access device including an anchor with a suture retention mechanism to help maintain its position relative to a patient during a surgical procedure.

BACKGROUND

In minimally invasive surgical procedures, including endoscopic and laparoscopic surgeries, a surgical access device permits the introduction of a variety of surgical instruments into a body cavity or opening. A surgical access device (e.g., a cannula) is introduced through an opening in tissue (i.e., a naturally occurring orifice or an incision) to provide access to an underlying surgical site in the body. The incision is typically made using an obturator having a blunt or sharp tip that has been inserted within the passageway of the surgical access device. For example, a cannula has a tube of rigid material with a thin wall construction, through which an obturator may be passed. The obturator is utilized to penetrate a body wall, such as an abdominal wall, or to introduce the surgical access device through the body wall, and is then removed to permit introduction of surgical instrumentation through the surgical access device to perform the surgical procedure.

During these procedures, it may be challenging to maintain the position of the surgical access device with respect to the body wall, particularly when exposed to a pressurized environment. To help maintain the position of the surgical access device with respect to the body wall, an anchor positioned near a distal end of the surgical access device and adjacent tissue is occasionally used. Positioning such an anchor while the surgical access device is within the body helps minimize undesired movement of the surgical access device with respect to the body.

Accordingly, it may be helpful to provide an anchor with a mechanism to help maintain the longitudinal position of the surgical access device with respect to the patient.

SUMMARY

The present disclosure relates to a surgical access device including a cannula body, an anchor, and a first suture retention mechanism. The cannula body includes a housing and an elongated portion extending distally from the housing. The elongated portion defines a longitudinal axis and a channel extending therethrough. The anchor is disposed in mechanical cooperation with the elongated portion of the cannula body and is longitudinally translatable relative to the elongated portion. The first suture retention mechanism extends laterally from the anchor. A suture-receiving channel is defined between a portion of the suture retention mechanism and a portion of the anchor.

In aspects, the suture-receiving channel may be ring-shaped.

In additional aspects, the first suture retention mechanism may include a cylindrical shoulder in contact with the anchor. The first suture retention mechanism may include a disc-shaped arm extending laterally from the cylindrical shoulder. The suture-receiving channel may be ring-shaped, it may surround the cylinder shoulder, and it may be disposed between the disc-shaped arm and the anchor.

In aspects, the surgical access device may include a second suture retention mechanism disposed in mechanical cooperation with the anchor. The second suture retention mechanism may be on an opposite side of the anchor from the first suture retention mechanism.

In additional aspects, the surgical access device may include a sleeve radially surrounding at least a portion of the elongated portion and disposed distally of the anchor. The sleeve may be made from foam, gel, or rubber.

The present disclosure also relates to a method of performing a surgical procedure. The method includes inserting a distal portion of a surgical access device into tissue, positioning a distal end of a sleeve engaged with an elongated portion of the surgical access device adjacent tissue, positioning a distal end of an anchor adjacent a proximal end of the sleeve, wrapping a suture at least partially around a suture retention mechanism engaged with the anchor, and inserting the suture through tissue.

In aspects, the method may include passing the suture through the sleeve. Wrapping the suture at least partially around the suture retention mechanism may occur prior to inserting the suture through tissue. The method may also include wrapping the suture at least partially around the suture retention mechanism after inserting the suture through tissue.

In additional aspects, wrapping the suture at least partially around the suture retention mechanism may include wrapping the suture at least partially around a cylindrical portion of the suture retention mechanism.

In aspects, wrapping the suture at least partially around the suture retention mechanism may include wrapping the suture 360° around a cylindrical portion of the suture retention mechanism.

In additional aspects, the method may include wrapping a second suture at least partially around a second suture retention mechanism engaged with the anchor. The method may further include inserting the second suture through tissue.

DESCRIPTION OF THE DRAWINGS

Various aspects of the present disclosure are illustrated herein with reference to the accompanying drawings, wherein.

DETAILED DESCRIPTION

Figure 1:
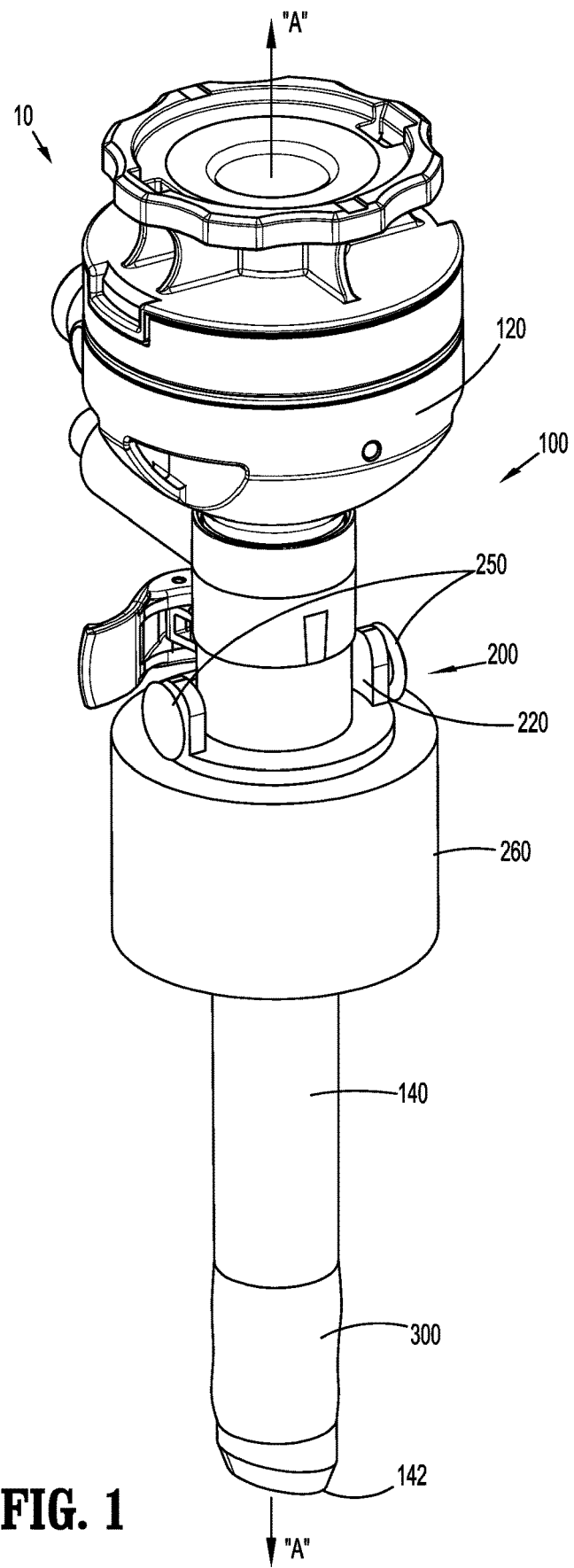
FIG. 1 is a perspective view of a surgical access device including an anchor in accordance with the present disclosure.

Aspects of the presently disclosed surgical access device will now be described in detail with reference to the drawings wherein like numerals designate identical or corresponding elements in each of the several views. As is common in the art, the term "proximal" refers to that part or component closer to the user or operator, i.e. surgeon or physician, while the term "distal" refers to that part or component farther away from the user.

Generally, the surgical access device or cannula, often part of a trocar assembly, may be employed during surgery (e.g., laparoscopic surgery) and may, in various aspects, provide for the sealed access of laparoscopic surgical instruments into an insufflated body cavity, such as the abdominal cavity. The cannula is usable with an obturator insertable therethrough. The cannula and obturator are separate components but are capable of being selectively connected together. For example, the obturator may be inserted into and through the cannula until the handle of the obturator engages, e.g., selectively locks into, a proximal housing of the cannula. In this initial position, the trocar assembly is employed to tunnel through an anatomical structure, e.g., the abdominal wall, either by making a new passage through the structure or by passing through an existing opening through the structure. Once the trocar assembly has tunneled through the anatomical structure, the obturator is removed, leaving the cannula in place in the structure, e.g., in the incision created by the trocar assembly. The proximal housing of the cannula may include seals or valves that prevent the escape of insufflation gases from the body cavity, while also allowing surgical instruments to be inserted into the body cavity.

Additionally, the surgical access device of the present disclosure includes an anchor including a suture retention mechanism. The anchor is configured to engage tissue to help maintain the cannula in its position relative to the body during use. The suture retention mechanism is configured to facilitate the securement of a suture to the anchor to help maintain the anchor in its position relative to the body during use.

FIGS. 1-11 illustrate a surgical access device according to the present disclosure. With initial reference to FIG. 1, the surgical access device 10 includes a cannula body 100 and an anchor 200. The cannula body 100 includes a proximal housing 120 at its proximal end, and includes an elongated portion 140 extending distally from the proximal housing 120. The elongated portion 140 defines a channel 150 (FIG. 2) extending therethrough, and defines a longitudinal axis "A-A." An obturator (not shown) is insertable through the channel 150 and is engageable with the proximal housing 120, for instance.

Figure 10:
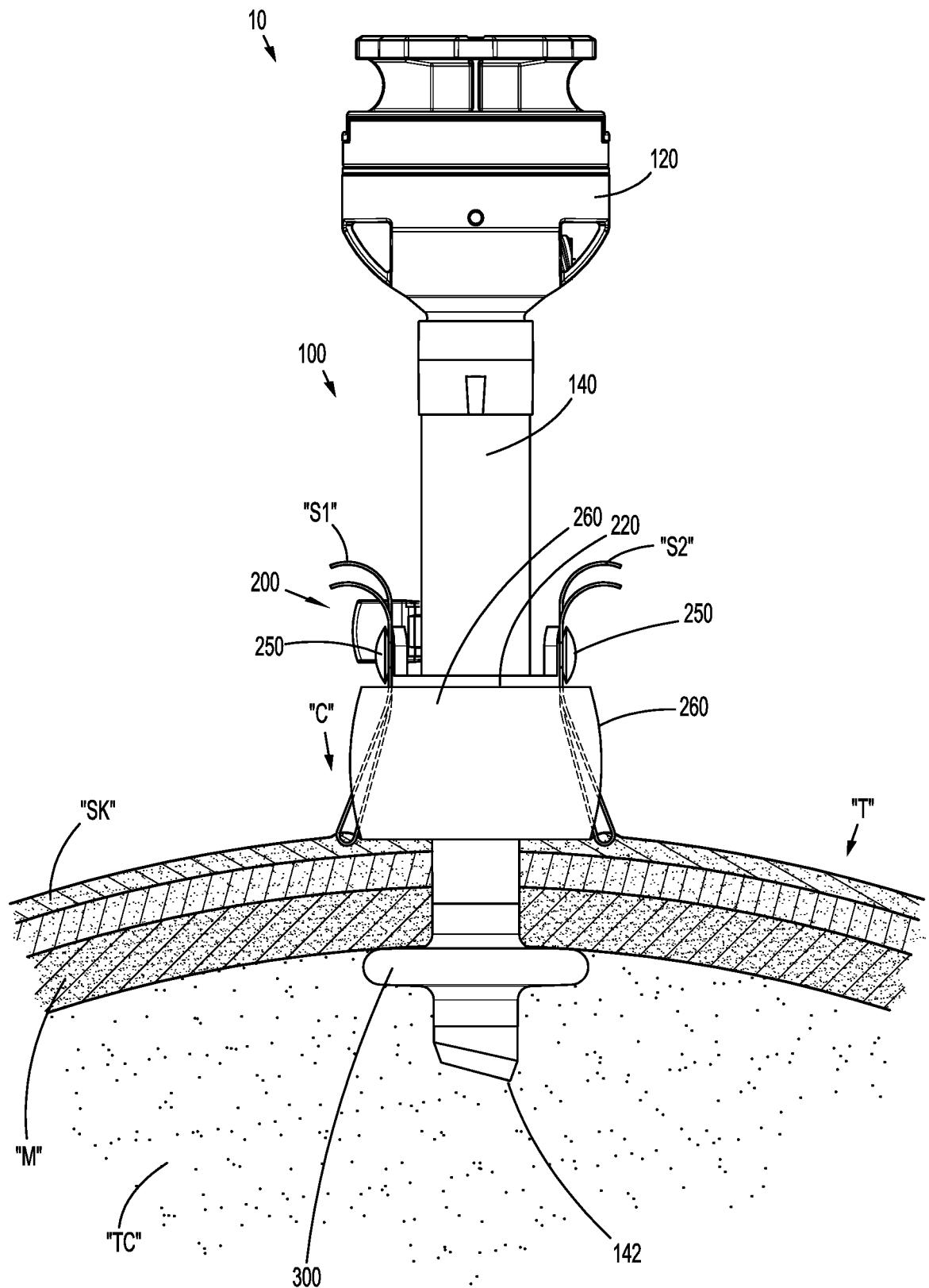
FIGS. 10 and 11 are side views of the surgical access device of FIGS. 1 and 2 showing portions within tissue, illustrating the anchor in a distal position, and illustrating sutures engaged with the suture retention mechanism, a portion of the anchor, and tissue.
Figure 11:
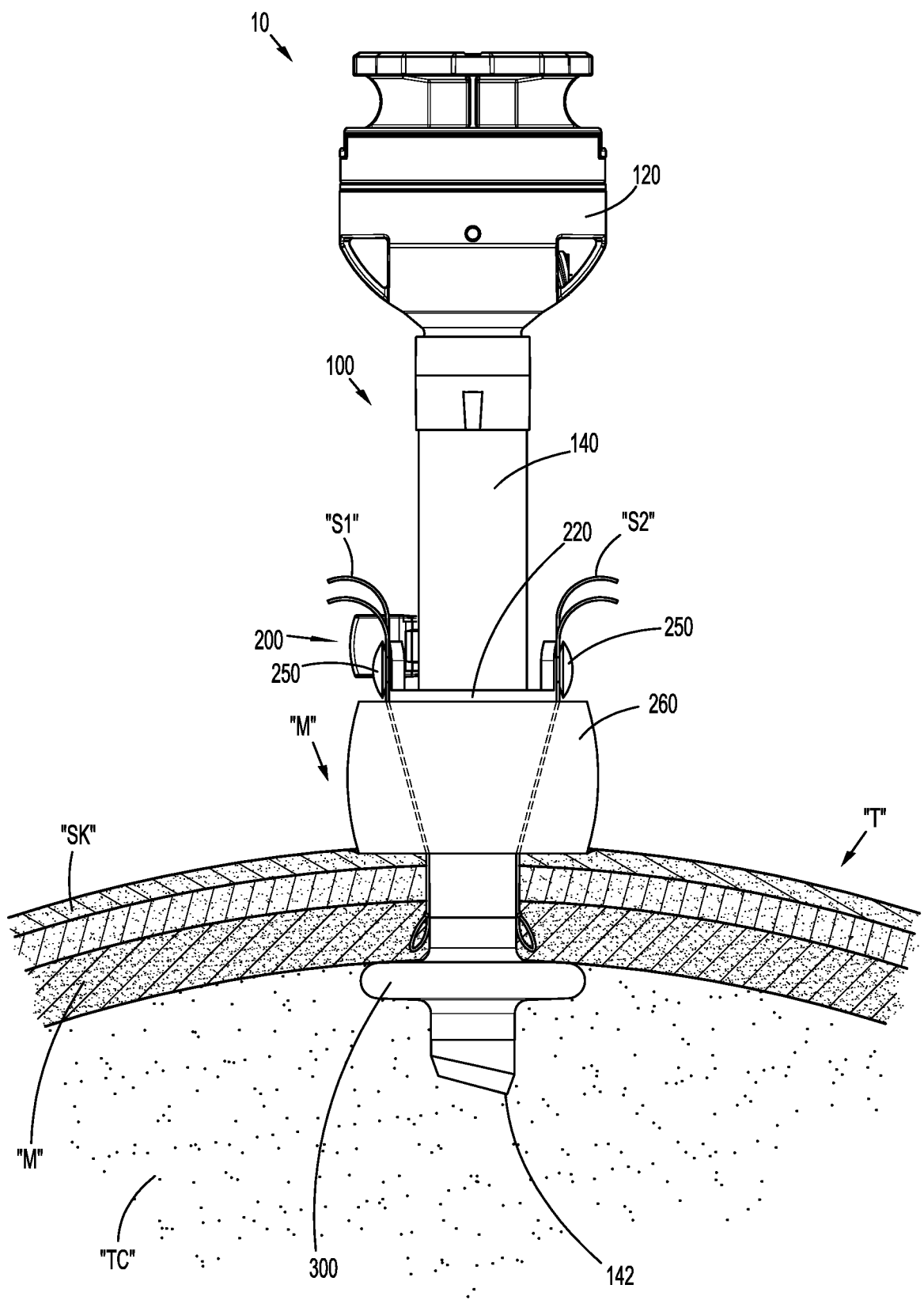

The anchor 200 is positionable around the elongated portion 140 of the cannula body 100 such that such that the anchor 200 radially surrounds a portion of the elongated portion 140. More particularly, the anchor 200 is longitudinally translatable along the elongated portion 140 between a first position, where the anchor 200 is farther away from a distal tip 142 of the elongated portion 140 (FIG. 1), and a second position, wherein the anchor 200 is closer to the distal tip 142 of the elongated portion 140 (FIGS. 10 and 11). Additionally, the anchor 200 is configured to releasably and selectively lock itself into a desired longitudinal position.

Figure 2:
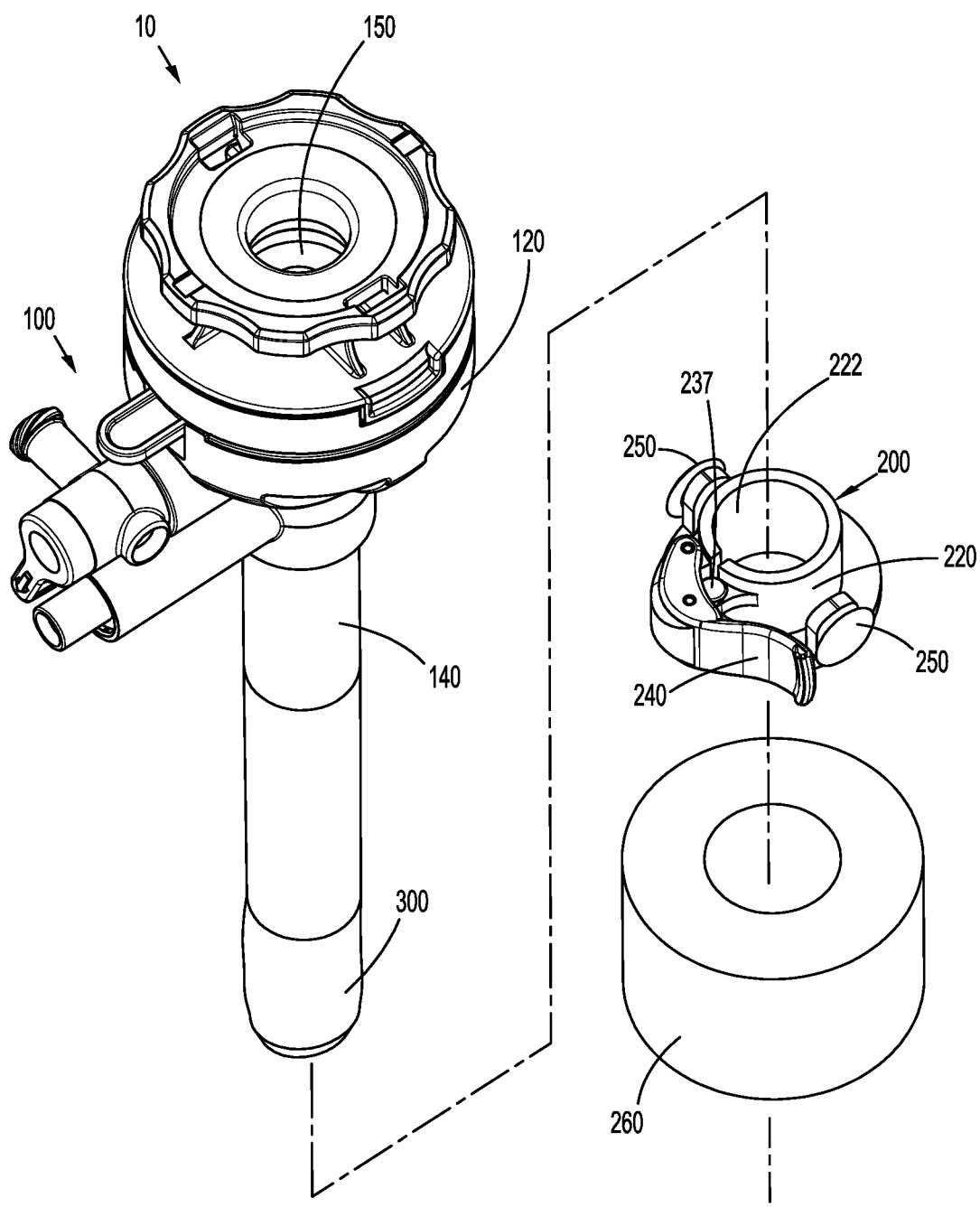
FIG. 2 is an assembly view of the surgical access device of FIG. 1.

Referring to FIGS. 1 and 2, the engagement between the anchor 200 and the cannula body 100 is shown. The anchor 200 includes a clip 220, and a handle 240. The clip 220 of the anchor 200 defines an aperture 222, through which the elongated portion 140 of the cannula body 100 is insertable.

Figure 3:
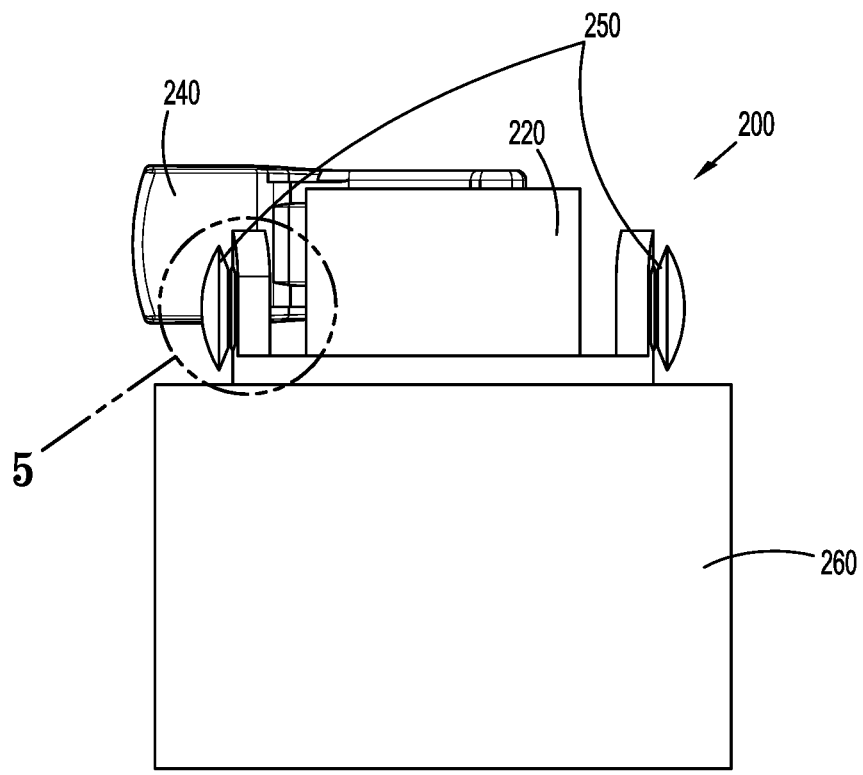
FIG. 3 is a side view of the anchor of FIGS. 1 and 2.
Figure 4:
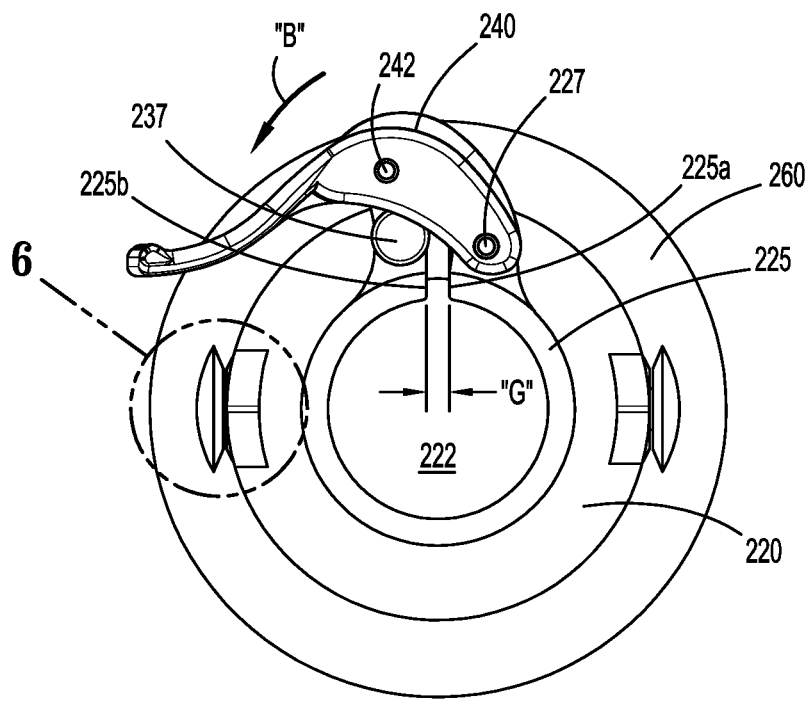
FIG. 4 is a top view of the anchor of FIGS. 1 and 2.

FIGS. 3 and 4 illustrate further details of the anchor 200 and the sleeve 260. The clip 220 of the anchor 200 includes an arcuate portion 225 having a first end 225a and a second end 225b. In aspects, the clip 220 may be C-shaped including an adjustable gap "G" defined between the first end 225a and the second end 225b of the arcuate portion 225. The first end 225a is movable relative to the second end 225b between a first orientation defining a first size, larger aperture and a second orientation defining a second size, smaller aperture. The gap "G" corresponding to the first size aperture is larger than the gap "G" corresponding to the second size aperture. In the first orientation, where the clip 220 defines a larger aperture, the anchor 200 is longitudinally translatable along the elongated portion 140 of the cannula body 100. In the second orientation, where the clip 220 defines a smaller aperture, the anchor 200 is fixed from translating longitudinally along the elongated portion 140 of the cannula body 100.

The handle 240 is movable to toggle the orientation of the clip 220. More particularly, and with particular reference to FIG. 4, the handle 240 is pivotable about a pivot pin 227 disposed adjacent the first end 225a of the arcuate portion 225. A handle pin 242 of the handle 240 is movable in the general direction of arrow "B" in FIG. 4 into engagement with a finger (e.g., a cam finger) 237 disposed adjacent the second end 225b of the arcuate portion 225. The engagement between the handle pin 242 and the finger 237 releasably locks the clip 220 into its second orientation corresponding to the smaller aperture; disengagement of the handle pin 242 and the finger 237 moves the clip 220 into its first orientation corresponding to the larger diameter. While a particular aspect is shown for releasably locking and unlocking the clip 220, other mechanisms are usable with the anchor 200 and are within the scope of the present disclosure.

Additionally, with reference to FIGS. 3-6, a suture retention mechanism 250 is shown engaged with the anchor 200. The suture retention mechanism 250 extends outwardly from the clip 220. While two suture retention mechanisms 250 are shown, the present disclosure contemplates an anchor having more or fewer than two suture retention mechanisms 250. Generally, the suture retention mechanisms 250 are usable as locations to tie sutures to during use, for instance.

Figure 5:
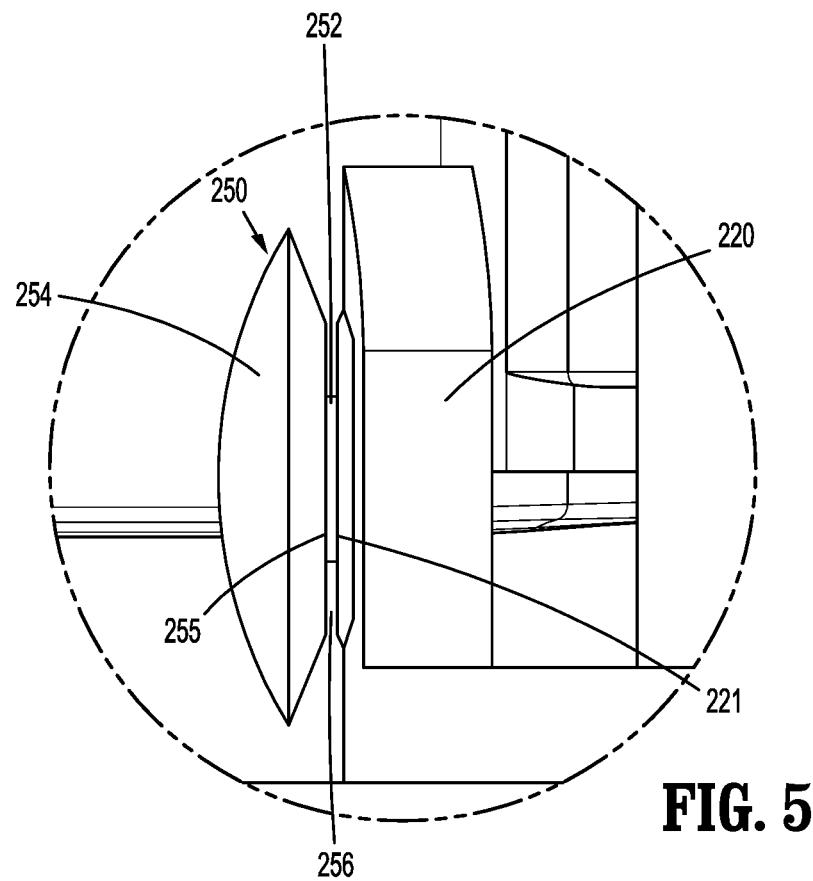
FIG. 5 is an enlarged view of the area of detail indicated in FIG. 3 illustrating a side view of the suture retention mechanism of the anchor.
Figure 6:
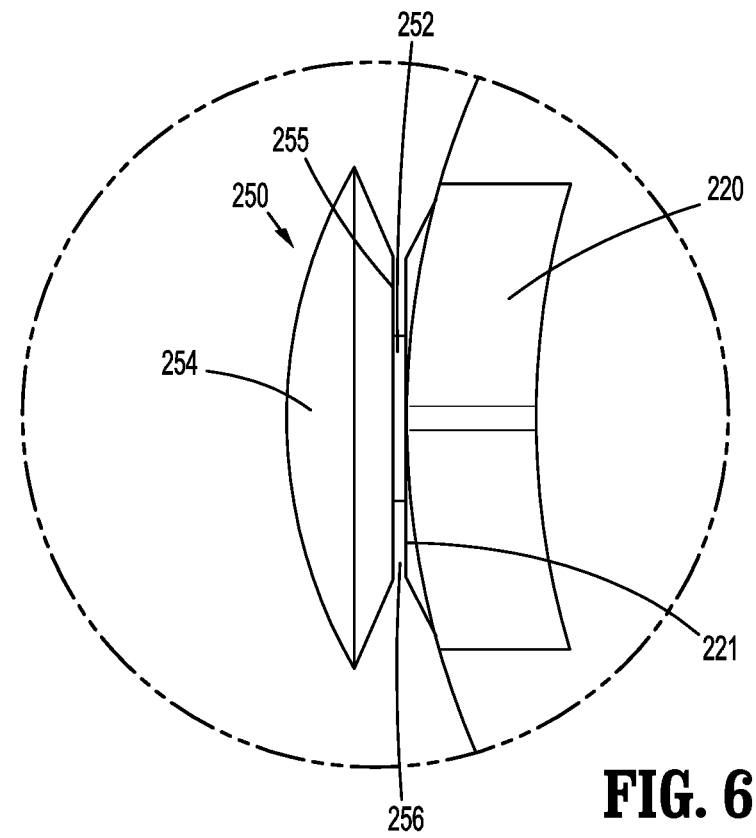
FIG. 6 is an enlarged view of the area of detail indicated in FIG. 4 illustrating a top view of the suture retention mechanism of the anchor.

With particular reference to FIGS. 5 and 6, the suture retention mechanism 250 includes a cylindrical shoulder 252 and a disc-shaped arm 254. The shoulder 252 extends laterally from the clip 220, and the arm 254 extends laterally from the shoulder 252. A ring-like, suture-receiving channel 256 is defined between an outer wall 221 of the clip 220 and an inner wall 255 of the arm 254; the shoulder 252 defines a radially inner boundary of the channel 256 and provides a smooth surface for engaging the suture "S."

Figure 9:
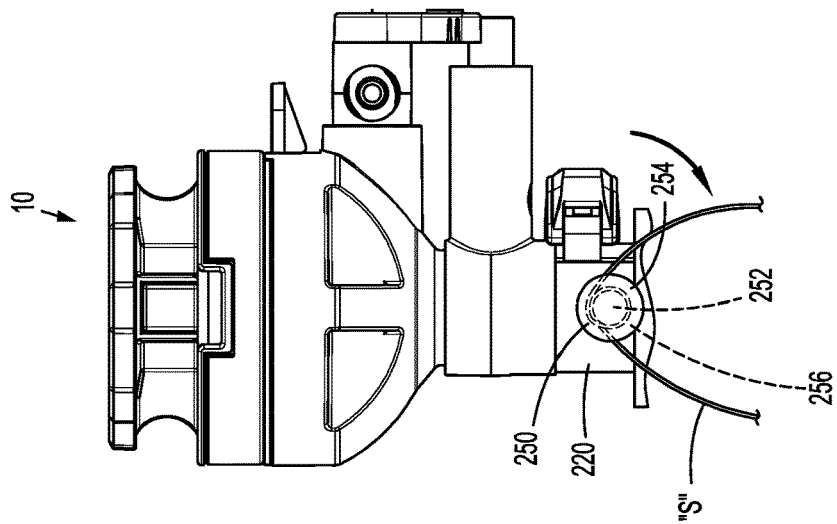
FIGS. 7-9 are side views of a portion of the surgical access device of FIGS. 1 and 2 showing various steps of wrapping a suture around a suture retention mechanism of the anchor.
Figure 8:
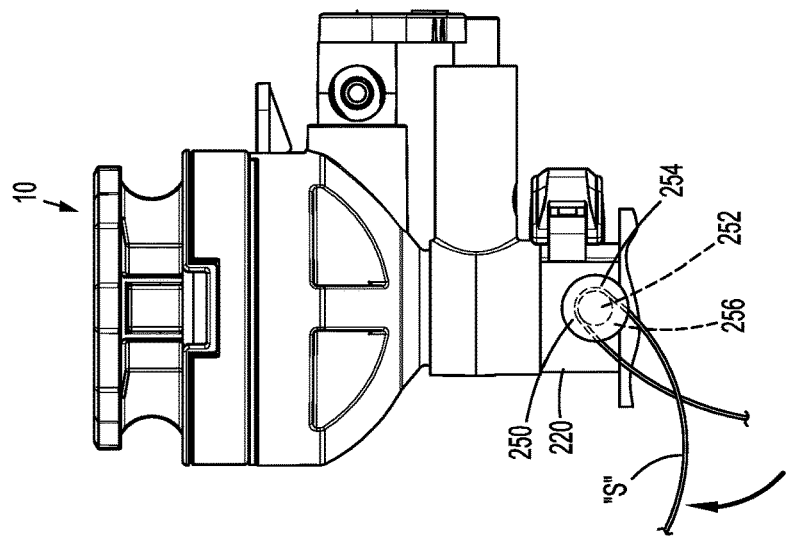
Figure 7:
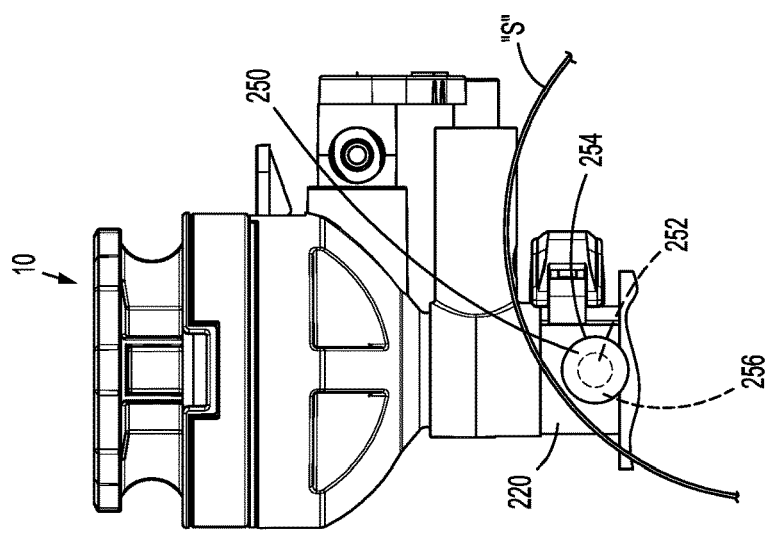

As shown in FIGS. 7-9, and as discussed in further detail below, during use of the surgical access device 10, a suture "S" can be wrapped around the shoulder 252 of the suture retention mechanism 250 such that part of the suture "S" is within the channel 256.

A sleeve 260 is shown in FIGS. 1-4, 10, and 11. In aspects, the sleeve 260 is secured to the clip 220 such that the sleeve 260 and the clip 220 cannot be moved independently of each other. In other aspects, the sleeve 260 and the anchor 200 are movable independently of each other. The sleeve 260 is configured to longitudinally compress in response to being moved against a tissue wall "T," for instance, as indicated by arrow "C" in FIGS. 10 and 11. The sleeve 260 may be made from foam, gel, rubber (e.g., elastomers), or another suitable compressive material.

Additionally, as shown in FIGS. 1, 2, 10, and 11, the anchor 200 can be used in connection with an additional fixation mechanism 300. For instance, as shown in FIGS. 10 and 11, while the anchor 200 may be positioned along the elongated portion 140 of the cannula body 100 adjacent a proximal wall of tissue "T" adjacent an incision, the fixation mechanism 300 can radially extend from the elongated portion 140 of the cannula body 100 using conventional methods and be positioned adjacent a distal wall of the tissue "T" adjacent the incision, for example.

Referring now to FIGS. 10 and 11, in use, the anchor 200 is initially in a proximal position along the elongated portion 140 of the cannula body 100 as the distal end of the cannula body 100 is being inserted into and/or positioned within the tissue cavity "TC." Next, the fixation mechanism 300, if included, is moved to its expanded position, and the cannula body 100 is moved proximally such that the fixation mechanism 300 contacts the distal portion of the tissue wall or muscle layer "M," for instance. Then, the anchor 200 and/or sleeve 260 is/are moved distally along the elongated portion 140 of the cannula body 100 such that the sleeve 260 contacts a proximal portion of the tissue wall or skin "S." Next, in aspects where the anchor 200 is separate from the sleeve 260, the anchor 200 is moved distally into contact with the sleeve 260. The handle 240 of the clip 220 is then utilized to decrease and lock the size of the aperture 222 such that the anchor 200 is fixedly positioned on the elongated portion 140 of the cannula body 100. Here, the tissue wall "T" is sandwiched between the sleeve 260 and the fixation mechanism 300, and the longitudinal position of the cannula body 100 is fixed relative to the tissue wall "T."

With continued reference to FIGS. 10 and 11, at least one suture "S" is used to further secure the anchor 200 to tissue "T." More particularly, the suture "S" is wrapped around the suture retention mechanism 250 (FIGS. 7-9), passed through (or around) the sleeve 260, passed through a layer of tissue "T," passed back through (or around) the sleeve 260, and wrapped around the suture retention mechanism 250 again. This additional securement using the suture "S" not only helps secure the position of the anchor 200 with respect to the tissue "T," but also helps keep the sleeve 260 in contact with the tissue "T" which may help to absorb bodily fluids, such as blood, that may exit the incision. In the aspect illustrated in FIGS. 10 and 11, a first suture "S1" is wrapped around one suture retention mechanism 250, and a second suture "S2" is wrapped around another suture retention mechanism 250.

In the aspect of FIG. 10, the sutures "S1" and "S2" are secured to an outer layer of tissue, e.g., the skin "SK." Here, after completion of the surgical procedure, the surgical access device 10 is removed from the incision, and the sutures "S1" and "S2" are also removed and discarded.

In the aspect of FIG. 11, the sutures "S1" and "S2" are secured to an inner layer of tissue, e.g., the muscle layer "M." Here, after completion of the surgical procedure, the sutures "S1" and "S2" are unwrapped from the suture retention mechanisms 250, the surgical access device 10 is removed from the incision, and the sutures "S1" and "S2" remain secured to the inner layer of tissue and are further used to help close the incision.

While the above description contains many specifics, these specifics should not be construed as limitations on the scope of the present disclosure, but merely as illustrations of various aspects thereof. Therefore, the above description should not be construed as limiting, but merely as exemplifications of various aspects. Those skilled in the art will envision other modifications within the scope and spirit of the claims appended hereto.

What is claimed is:

1. A surgical access device, comprising:
   a cannula body including a housing and an elongated portion extending distally from the housing, the elongated portion defining a longitudinal axis and a channel;
   an anchor disposed in mechanical cooperation with the elongated portion of the cannula body and being longitudinally translatable relative to the elongated portion;
   a first suture retention mechanism extending laterally from the anchor, wherein a suture-receiving channel is defined between a portion of the first suture retention mechanism and a portion of the anchor; and
   a foam sleeve radially surrounding at least a portion of the elongated portion of the cannula body and disposed distally of the anchor.

2. The surgical access device according to claim 1, wherein the suture-receiving channel is ring-shaped.

3. The surgical access device according to claim 1, wherein the first suture retention mechanism includes a cylindrical shoulder in contact with the anchor.

4. The surgical access device according to claim 3, wherein the first suture retention mechanism includes a disc-shaped arm extending laterally from the cylindrical shoulder.

5. The surgical access device according to claim 4, wherein the suture-receiving channel is ring-shaped, the suture-receiving channel surrounds the cylinder shoulder, and the suture-receiving channel is disposed between the disc-shaped arm and the anchor.

6. The surgical access device according to claim 3, wherein the suture-receiving channel surrounds the cylindrical shoulder.

7. The surgical access device according to claim 1, further including a second suture retention mechanism disposed in mechanical cooperation with the anchor.

8. The surgical access device according to claim 7, wherein the second suture retention mechanism is on an opposite side of the anchor from the first suture retention mechanism.

9. The surgical access device according to claim 1, wherein the foam sleeve extends farther from the longitudinal axis than the first suture retention mechanism.

10. The surgical access device according to claim 1, wherein the foam sleeve is configured to be passed through by a suture.

11. A surgical access device, comprising:
    a cannula defining a longitudinal axis;
    an anchor disposed in mechanical cooperation with the cannula and being longitudinally translatable relative to the cannula;
    a first suture retention mechanism extending laterally from the anchor, wherein a suture-receiving channel is defined between a portion of the first suture retention mechanism and a portion of the anchor; and
    a sleeve extending distally from the anchor, wherein the sleeve extends farther from the longitudinal axis than the first suture retention mechanism.

12. The surgical access device according to claim 11, wherein the sleeve is configured to be passed through by a suture.

13. The surgical access device according to claim 11, wherein the sleeve is made from foam.

14. The surgical access device according to claim 11, wherein the suture-receiving channel is ring-shaped.

15. The surgical access device according to claim 11, wherein the first suture retention mechanism includes a cylindrical shoulder in contact with the anchor.

16. The surgical access device according to claim 15, wherein the first suture retention mechanism includes a disc-shaped arm extending laterally from the cylindrical shoulder.

17. The surgical access device according to claim 16, wherein the suture-receiving channel is ring-shaped, the suture-receiving channel surrounds the cylinder shoulder, and the suture-receiving channel is disposed between the disc-shaped arm and the anchor.

18. The surgical access device according to claim 15, wherein the suture-receiving channel surrounds the cylindrical shoulder.

19. The surgical access device according to claim 11, further including a second suture retention mechanism disposed in mechanical cooperation with the anchor.

20. The surgical access device according to claim 19, wherein the second suture retention mechanism is on an opposite side of the anchor from the first suture retention mechanism.

* * * * *